United States Patent
Camus et al.

(10) Patent No.: US 8,620,408 B2
(45) Date of Patent: Dec. 31, 2013

(54) METHOD FOR REPRESENTING TWO-DIMENSIONAL PROJECTION IMAGES AND OBJECTS CORRESPONDING THERETO

(75) Inventors: Estelle Camus, Mountain View, CA (US); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 1280 days.

(21) Appl. No.: 11/809,275

(22) Filed: May 31, 2007

(65) Prior Publication Data

US 2008/0033285 A1     Feb. 7, 2008

(30) Foreign Application Priority Data

May 31, 2006   (DE) .......................... 10 2006 025 420

(51) Int. Cl.
     *A61B 5/055*      (2006.01)

(52) U.S. Cl.
USPC ........... 600/425; 600/481; 600/507; 600/415; 382/130; 382/162; 382/128

(58) Field of Classification Search
USPC .......... 382/169, 294, 162, 130, 128; 600/425, 600/507, 2, 415, 48, 481, 431, 407, 504, 600/411
See application file for complete search history.

(56) References Cited

U.S. PATENT DOCUMENTS

| | | | |
|---|---|---|---|
| 5,636,636 A * | 6/1997 | Kuhn et al. .................... | 600/415 |
| 6,507,668 B1 * | 1/2003 | Park .............................. | 382/169 |
| 7,492,856 B2 * | 2/2009 | Garms et al. .................. | 378/15 |
| 7,572,230 B2 * | 8/2009 | Neumann et al. ............. | 600/504 |
| 7,664,543 B2 * | 2/2010 | Gordon ......................... | 600/431 |
| 7,774,041 B2 * | 8/2010 | Nambu et al. ................. | 600/407 |
| 2003/0055328 A1 * | 3/2003 | Paladini ........................ | 600/407 |
| 2003/0097076 A1 * | 5/2003 | Nambu et al. ................. | 600/504 |
| 2003/0114759 A1 | 6/2003 | Skyba et al. | |

(Continued)

FOREIGN PATENT DOCUMENTS

| | | |
|---|---|---|
| DE | 100 00 185 A1 | 7/2001 |
| DE | 101 00 572 A1 | 7/2002 |

(Continued)

OTHER PUBLICATIONS

Thomas Wittenberg, Peter Hastreiter, Ulrich Hoppe, Heinz Handels, Alexander Horsch and Hans-Peter Meinzer, "Quantitative Analyse von Koronarangiographischen Bildfolgen zur Bestimmung der Myokardperfusion", Bildverareitung für die Medizin 2003, Proceedings des Workshops, vol. 9, Mar. 11, 2003, Erlangen, Germany, pp. 81-85.

*Primary Examiner* — Mekonen Bekele

(57) ABSTRACT

2-D projection images show the variation over time of the distribution of a contrast medium in an examination subject. Each projection image comprises pixels having pixel values corresponding to one another in the projection images that are determined by identical areas of the examination subject. A computer subdivides an image that is to be displayed from the projection images into parcels in one perfusion region. For each parcel, the computer determines a characteristic value and, based on the characteristic value, a projection color. It assigns the projection color to the parcel. The characteristic value is determined based on the pixel values occurring in the parcel of the projection image or their differences from the pixel values of a corresponding parcel of another projection image. The computer outputs a subarea of the projection image containing the perfusion region. It represents each parcel of the perfusion region in its assigned projection color.

20 Claims, 13 Drawing Sheets

(56) References Cited

U.S. PATENT DOCUMENTS

| | | |
|---|---|---|
| 2005/0020945 A1* | 1/2005 | Tosaya et al. ............. 601/2 |
| 2005/0111757 A1* | 5/2005 | Brackett et al. ............ 382/294 |
| 2005/0113680 A1* | 5/2005 | Ikeda et al. ............... 600/425 |
| 2006/0004279 A1* | 1/2006 | Ikeda et al. ............... 600/411 |
| 2006/0241402 A1* | 10/2006 | Ichihara et al. ............ 600/425 |
| 2007/0140415 A1* | 6/2007 | Garms et al. .............. 378/19 |

FOREIGN PATENT DOCUMENTS

| | | |
|---|---|---|
| DE | 102005018327 A1 | 10/2006 |
| DE | 10 2005 039 189 A1 | 2/2007 |
| EP | 1 302 163 A2 | 4/2003 |
| EP | 1 585 058 A2 | 10/2005 |
| WO | WO 97/17673 A1 | 5/1997 |

* cited by examiner

| | Object vessel | (Grayscale 1) |
| | Object background | (Grayscale 2) |
| | Perfusion low | (Projection color 1) |
| | Perfusion medium | (Projection color 2) |
| | Perfusion high | (Projection color 1) |

| | Object vessel | (Grayscale value 1) |
| --- | --- | --- |
| | Object background | (Grayscale value 2) |
| | Perfusion low | (Evaluation color 1) |
| | Perfusion medium | (Evaluation color 1) |
| | Perfusion high | (Evaluation color 1) |

METHOD FOR REPRESENTING TWO-DIMENSIONAL PROJECTION IMAGES AND OBJECTS CORRESPONDING THERETO

CROSS REFERENCE TO RELATED APPLICATIONS

This application claims priority of German application No. 10 2006 025 420.1 filed May 31, 2006, which is incorporated by reference herein in its entirety.

FIELD OF THE INVENTION

The present invention relates to a method for representing two-dimensional projection images which show the variation over time of the distribution of a contrast medium in an examination subject, the examination subject containing a vascular system and its surroundings, each projection image comprising a plurality of pixels having pixel values, the pixel values of pixels corresponding to one another in the projection images being determined by at least essentially locally identical areas of the examination subject.

BACKGROUND OF THE INVENTION

Representation methods of this kind and the corresponding objects are known.

Thus, for example, a representation method of this kind is known from the technical article "Quantitative Analyse von koronarangiographischen Bildfolgen zur Bestimmung der Myokardperfusion" ("*Quantitative analysis of coronary angiographic image sequences for determining myocardial perfusion*") by Urban Malsch et al., published in "Bildverarbeitung für die Medizin 2003—Algorithmen—Systeme—Anwendungen" ("*Image processing for medicine 2003—algorithms—systems—applications*"), Springer Verlag, pages 81 to 85. With this representation method a computer determines a two-dimensional evaluation image comprising a plurality of pixels on the basis of the projection images and outputs the evaluation image to a user via a display device. The pixels of the evaluation image correspond to those of the projection images. Based on the variation over time of the pixel values of the projection images, the computer assigns a pixel value to the pixels of the evaluation image, the pixel value being characteristic of the time of the maximum change in contrast.

The teaching of the above-cited technical article is described in the context of angiographic examinations of the coronary vessels of the human heart. This type of examination is one of the most important diagnostic tools in cardiology today. Additional information such as determining the flow rate or myocardial perfusion is further information which can be obtained in principle by means of angiography. The essential diagnostic finding is the perfusion of the myocardium.

Further noninvasive examination methods such as PET, SPECT, MR or contrast-medium-based ultrasound are known in the prior art. In addition to other parameters, these examination methods also enable the perfusion status of the myocardium to be quantified. These methods are generally applied in stable angina pectoris cases or for risk assessment following a myocardial infarction.

For an assessment of the therapeutic outcome of an intervention it would be advantageous to be able to monitor the improvement in perfusion or, as the case may be, the occurrence of microembolization and microinfarctions during the actual intervention. It would therefore be advantageous if a quantification of the perfusion were added to other diagnostic parameters already in the catheter laboratory, as this would enable all the relevant information to be obtained in one examination and thus to achieve an improvement in the monitoring of treatment.

However, quantifying the perfusion of the myocardium using angiographic methods is problematical, since the angiographically observable cardiac vessels have a diameter of barely a millimeter or more. These observable vessels terminate in millions of tiny capillary vessels which have diameters of only a few micrometers. The flow dynamics and distribution in the capillary vessels are ultimately determined by the blood supply of the cardiac muscle. Drawing conclusions about the dynamics of perfusion in the capillary vessels from the macroscopic perfusion is therefore, strictly speaking, inadmissible, even though it is often practiced.

Various methods for recording the perfusion of the myocardium are known, in particular contrast echocardiography, magnetic resonance tomographic diagnostics and SPECT.

The echocardiographic determination of global and regional function is an integral component of noninvasive cardial functional diagnosis. Dynamic and pharmacological stress echo cardiography are used in particular in cases of ischemia and in vitality diagnostics and contribute toward indicating revascularizing measures in the case of chronic coronary heart diseases. Recently introduced contrast-specific imaging methods enable the signal from the intramyocardial blood pool to be amplified and on the basis thereof deductions can be made with regard to the myocardial perfusion. Current realtime methods even enable the simultaneous assessment of wall motion and myocardial perfusion at a high spatial resolution.

Magnetic resonance tomographic diagnostic methods for coronary heart diseases are based on the evidence of pharmacologically induced perfusion or wall-motion disorders. Contrast-medium-based first-pass perfusion measurement at rest and under pharmacological stress is the preferred procedure today for assessing myocardial perfusion. Here, drugs are used which lead to dilation of the unaffected coronary arteries and consequently, due to the raised blood flow in these dilated coronary arteries, result in an increase of the lower perfusion rate in the area supplied by a stenosed coronary artery.

SPECT is a nuclear medicine technique. Tc-99m is nowadays used for this purpose as a contrast medium in addition to thallium-201 chloride. Myocardial perfusion scintigraphy records the perfusion of the cardiac muscle under ergometric and pharmacological stress and at rest. In the process reversible ischemias can be differentiated from permanent perfusion disorders or myocardial scars. A prerequisite for this method is an optimized tomographic examination technology.

Acute myocardial infarction represents a cardiological emergency situation in which rapid diagnosis and treatment are required. In this type of emergency situation an examination of the patient using magnetic resonance tomographic methods, SPECT methods or contrast echo cardiography is generally not possible. Further problems arise if for different reasons it was not possible to carry out a perfusion measurement in advance. In all these cases angiographically based cardiac perfusion imaging would represent an important tool.

In angiographically based cardiac perfusion imaging, long recordings are made, the recordings lasting until such time as the contrast medium has flowed through the coronary vessels and is visible in the myocardium itself. This last-mentioned phase is referred to as "myocardial blush". Assessment of the "myocardial blush" serves to provide evidence of the vascular supply to the heart and for example to rate the success of treatments and/or a risk profile for the patient.

In order to make the blood flow dynamics in large vessels and in the capillary vessels measurable and thereby comparable, various gradation systems are known which divide up the continuum of conditions into discrete classes. Some of these classifications describe the macroscopic circulation of blood, others the circulation of blood in the capillaries. The most-used classifications were drawn up by the scientific organization "Thrombolysis in Myocardial Infarction" (TIMI). These classifications are regarded as the de facto standard. The TIMI classifications are frequently used in multi-center studies in which the primary objective is to obtain reproducible and comparable results. However, the classifications are complex and time-consuming to apply. They are therefore not generally used in routine clinical work.

By far the most frequently used method in the prior art is visual assessment of the "myocardial blush" on the screen. This procedure is often used for multi-center studies. A prerequisite for this procedure is that the angiographic recording is long enough in order to be able to see the entry and washout of the contrast medium. However, the visual assessment requires a great deal of experience and is in practice carried out only by TIMI blush experts, as they are known.

There are also various procedures known in which an attempt is made to carry out the subjective-personal visual assessment with the aid of computers. An example can be found in the above-cited technical article by Urban Malsch et al.

The procedure in the above-cited technical article represents a good initial approach but still has shortcomings. Thus, for example, it is necessary in particular to identify the vessels of the vascular system in the projection images in order to mask out these vessels when analyzing the "myocardial blush". With the procedure presented in the technical article it is also necessary to work with DSA images. This creates a significant risk of artifacts, so that compute-intensive motion compensation methods are in turn required in order to avoid said artifacts.

Image evaluation methods for two-dimensional projection images are also described in the German patent application DE 10 2005 039 189.3. On the day of filing of the present invention the cited patent application is not yet publicly accessible and therefore does not represent a general prior art. This patent application is to be taken into account in the process of the examination as to novelty only in the German patent granting procedure.

The approach disclosed in DE 10 2005 039 189.3 is already very good. The color-coded representation of the parcel type (vessel, perfusion region, background) and the extent (degree of perfusion) also results in a good detectability of the perfusion determined in the context of DE 10 2005 039 189.3. On the other hand, the approach described in DE 10 2005 039 189.3 is not suitable for direct detectability of the perfusion of the examination subject, in other words for the visual assessment of the blush.

SUMMARY OF THE INVENTION

The object of the present invention is to provide a method for representing two-dimensional projection images of the type cited in the introduction which permits good visual detectability of perfusion in a simple manner.

The object is achieved by means of a representation method having the features recited in the claims.

The following is provided according to the invention:

Out of the projection images, a computer subdivides a projection image that is to be displayed into parcels at least in a perfusion region.

For each parcel contained in the perfusion region, the computer determines at least one characteristic value and, on the basis of the at least one characteristic value, a projection color. It assigns the projection color to the respective parcel.

For each parcel, the computer determines the at least one characteristic value based on the pixel values occurring in the respective parcel of the projection image that is to be displayed. Alternatively the computer can determine for each parcel the at least one characteristic value based on the pixel values occurring in the respective parcel of the projection image that is to be displayed and their differences from the pixel values of a corresponding parcel of another projection image.

From the projection image that is to be displayed, the computer outputs at least one subarea containing the perfusion region to a user via a display device. It represents each parcel of the perfusion region of the projection image to be displayed in its assigned projection color.

Because of the color assignment there is a substantial improvement in the detectability of the perfusion compared to a grayscale representation. By subdividing into parcels it is possible to avoid too strong a scattering of the color values in a narrow space.

The representation method according to the invention is universally applicable. It is therefore applicable in particular also where the examination subject does not move. An example of such an examination subject is the human brain, in which the same perfusion problems can occur as in the human heart. Said perfusion problems are known, where they occur acutely, by the term "stroke". As a general rule, however, the examination subject is an iteratively moving examination subject. In this case a series of images is first captured and supplied to the computer. Phase information relating to the examination subject is assigned to each image of the series. The projection images are selected from this series, care being taken to ensure that the phase information assigned to the projection images deviates by no more than one phase boundary from a reference phase. Both the reference phase and the phase boundary can be predefined for the computer by the user.

The computer preferably represents the part of the projection image to be displayed that lies outside of the perfusion region in black/white or as a grayscale image. Restricting the color coding to the perfusion region thus enhances the detectability of the perfusion for the user.

The computer preferably also subdivides the part of the projection image to be displayed that lies outside of the perfusion region into parcels and assigns each of the parcels of the projection image to be displayed that are located outside of the perfusion region either a grayscale value or one of the values black or white.

It is possible that the perfusion region is specified to the computer by the user. It is equally possible for the computer to determine the perfusion region automatically.

In the case of automatic determination of the perfusion region, the computer preferably determines, at least for each pixel of the subarea on the basis of the variation over time of the pixel values of those pixels of the projection images which lie in a two-dimensional evaluation core of the projection images that is determined by the respective pixel and is uniform for all projection images, whether the respective pixel belongs to the perfusion region.

It is most particularly preferred that for each pixel the computer determines as the evaluation core the parcel in which the relevant pixel lies. By means of this measure the computational overhead can be minimized.

In a further embodiment of the present invention the computer adds the pixel values of the pixels lying in the perfusion region of the displayed projection image or their differences from the pixel values of the pixels lying in the perfusion region of the other projection image to form an overall perfusion. Based on the overall perfusion the computer in this case preferably determines at least one characteristic quantity of an acoustic signal and outputs the acoustic signal via a loudspeaker together with the subarea of the displayed projection image. In particular the volume, the duration and most preferably the frequency of the acoustic signal are suitable as a characteristic quantity of the acoustic signal.

The characteristic value lies between a minimum value and a maximum value. The projection color preferably consists of a first color in a first proportion and of a second color for the remainder. The first proportion is preferably a monotonous function of the characteristic value. These measures improve the detectability of the perfusion.

The intuitive assignment of a perfusion to a particular color is particularly easy for the user if the first and the second color are primary colors, that is to say are defined from the group of colors made up of yellow, red and blue. The color combination yellow and red in particular has proven particularly advantageous in trials.

If it is intended to form a difference between the pixel values of the projection image to be displayed and those of the other projection image, the other projection image is preferably the first projection image in time sequence. In particular no contrast medium or at least only a small amount of contrast medium is usually present in the chronologically first projection image.

The computer preferably outputs the projection images one after the other via the display device according to their chronological sequence. This allows the user a particularly easy evaluation. It is particularly advantageous if the output of the projection images one after the other according to their chronological sequence is combined with the output of the acoustic signal.

The computer preferably assigns, at least in the perfusion region, a degree of perfusion to the parcels of an evaluation image corresponding to the projection images, assigns an evaluation color to the parcels of the evaluation image on the basis of the degree of perfusion, outputs at least one subarea of the evaluation image containing the perfusion region to the user via the display device and represents each parcel of the perfusion region of the evaluation image in its assigned evaluation color.

Outside of the perfusion region it is preferred—analogously to the procedure in the case of projection images that are to be displayed—that the computer represents the evaluation image in black/white or as a grayscale image. In particular the computer can also subdivide the evaluation image outside of the perfusion region into parcels and assign a grayscale value or one of the values black or white to each of the parcels of the evaluation image that lie outside of the perfusion region.

It is possible for the computer to overlay the evaluation image with the pixel values of one of the projection images. Insofar as the overlaying with the evaluation image is concerned, therefore, this projection image is represented as it is. No parcel forming of the projection image takes place with regard to the overlaying.

When an overlaying of a projection image takes place, that projection image in which the proportion of the vessels filled with contrast medium is at a maximum is preferably used for this purpose. Where applicable, said projection image can be determined automatically by the computer.

BRIEF DESCRIPTION OF THE DRAWINGS

Further advantages and details will emerge from the following description of exemplary embodiments in conjunction with the schematic drawings, in which.

DETAILED DESCRIPTION OF THE INVENTION

Figure 1:
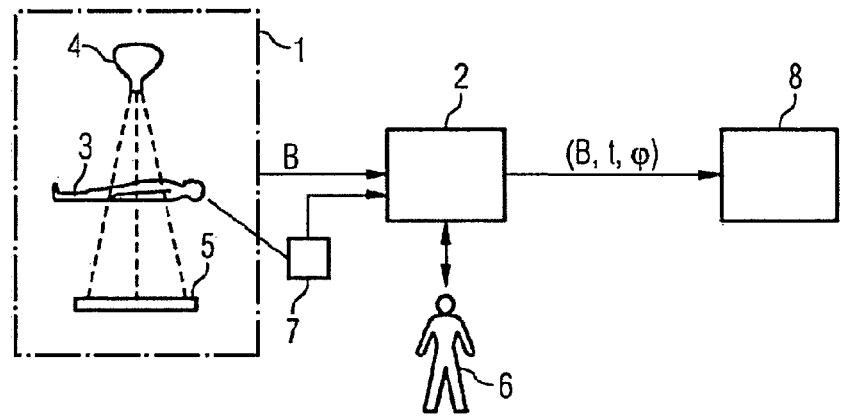
FIG. 1 shows a block diagram of a recording arrangement, a control computer and an evaluation device.

Referring to FIG. 1, a recording arrangement 1 is controlled by a control device 2. Images B of an examination subject 3 are captured by means of the recording arrangement 1. In the present case, in which the examination subject 3 is a person, images B of the heart or of the brain of the person 3 are captured, for example.

For the purpose of capturing the images B the recording arrangement 1 has a radiation source 4, in this case, for example, an X-ray source 4, and a corresponding detector 5.

Figure 2:
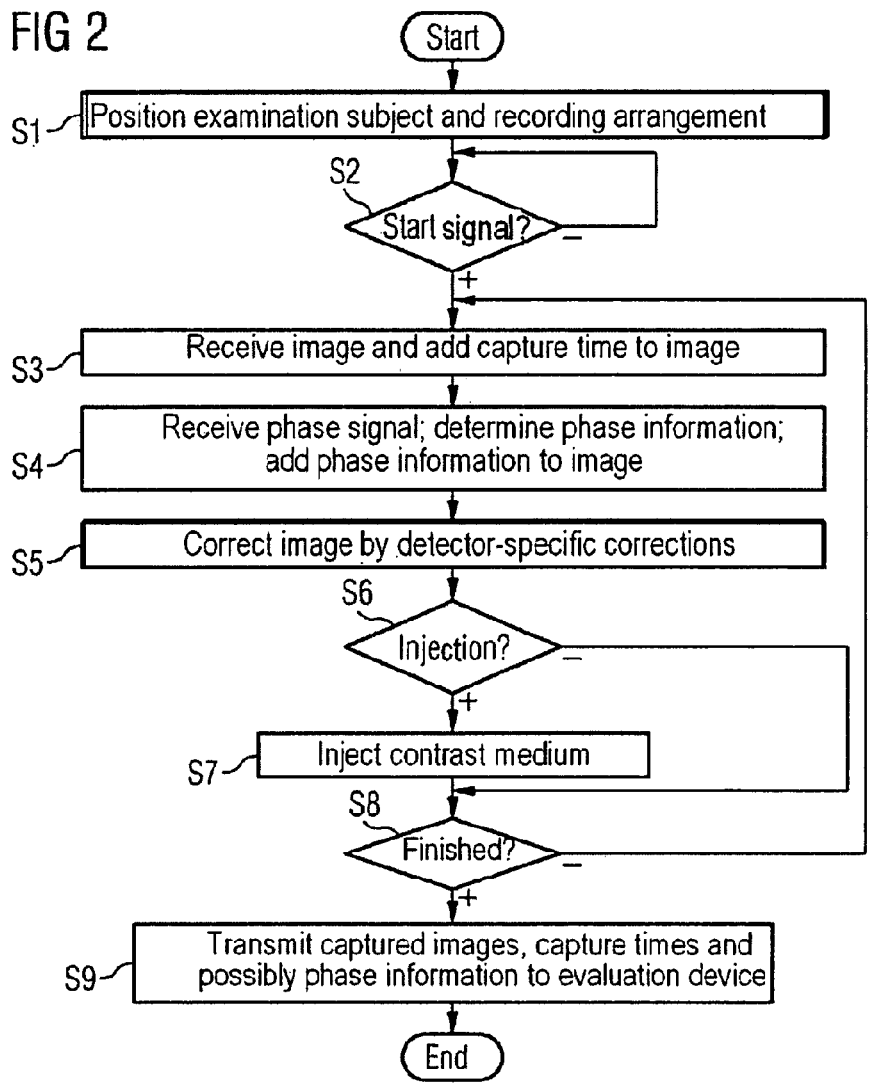
FIG. 2 is a flowchart.

Referring to FIG. 2, the examination subject 3 and the recording arrangement 1 are positioned in a step S1 for the purpose of capturing the images B. The positioning can be dependent in particular on which region (heart, brain, . . . ) of the examination subject 3 is to be recorded and which part of the region is especially relevant, for example which coronary artery (RCA, LAD, LCX) is to be observed. Step S1 can alternatively be performed purely manually by a user 6, fully automatically by the control device 2 or else by the user 6 with the support of the control device 2.

Step S1 can be performed in conjunction with a recording of control images. This is not relevant in the context of the present invention and will therefore not be explained in more detail.

In a step S2, the control device 2 waits for a start signal of the user 6. After the start signal has been received, the detector 5 captures an image B of the examination subject 3 and supplies it to the control device 2. The control device 2 receives the image B in a step S3 and adds a corresponding capture time t to the image B. If the examination subject 3 or the relevant part of the examination subject 3 were to move iteratively, in a step S4 the control device 2 also receives a phase signal of the examination subject 3 from a corresponding recording device 7.

Also in the course of step S4, the control device 2 determines corresponding phase information $\phi$ and adds said phase information $\phi$ to the captured image B. In the course of step S4 the control device 2 can, for example, receive an ECG signal and from it derive the phase information $\phi$. The control device 2 can also control the recording arrangement 1 with the aid of the supplied phase signal where necessary in such a way that already the capturing of the images B takes place only at one or more predefined phase positions of the examination subject 3, for example only 0.3 and 0.6 seconds after the R wave of the ECG signal.

Generally, the examination subject 3 is not influenced in its iterative motion by external factors. If, for example, the heart of the person 3 is beating very irregularly, an external stimulation of the heart can be performed in a targeted manner by means of a cardiac pacemaker in order to enforce a regular heartbeat.

In a step S5, the control device 2 corrects the captured image B. The control device 2 preferably corrects the captured image B exclusively by detector-specific corrections but does not perform any more extensive image editing. It does not, for example, apply any noise-reduction methods.

In a step S6, a check is carried out to establish whether a contrast medium is to be injected. If this check is answered in the affirmative, the contrast medium is injected into the examination subject 3 in a step S7. As in step S1, steps S6 and S7 can be performed by the user 6 independently, fully automatically by the control device 2 or else by the user 6 with the support of the control device 2.

In a step S8, the control device 2 checks whether the capturing of the images B is to be terminated. If this is not the case, the control device 2 goes back to step S3. Otherwise it transmits in a step S9 the captured images B, preferably corrected by detector-specific corrections, their capture times t and where applicable also their phase information $\phi$ to an evaluation device 8. As an alternative to transmission of the images B, the capture times t and the phase information $\phi$ as part of the downstream step S9, the transmission could be carried out image by image, i.e. between steps S5 and S6.

The method outlined above has been sketched out only roughly, as it is of only secondary importance within the scope of the present invention. Thus, for example, the—manual, fully automatic or computer-aided—setting of the recording parameters of the recording arrangement 1 (operating voltage of the radiation source 4, image rate, image preprocessing, positioning, etc.) was taken as self-evident. Any calibration of the recording arrangement 1 which may be necessary can also be carried out. It also goes without saying that the images B must be captured over a sufficiently long period, namely starting before the injection of the contrast medium and ending after the washout of the contrast medium.

Figure 3:
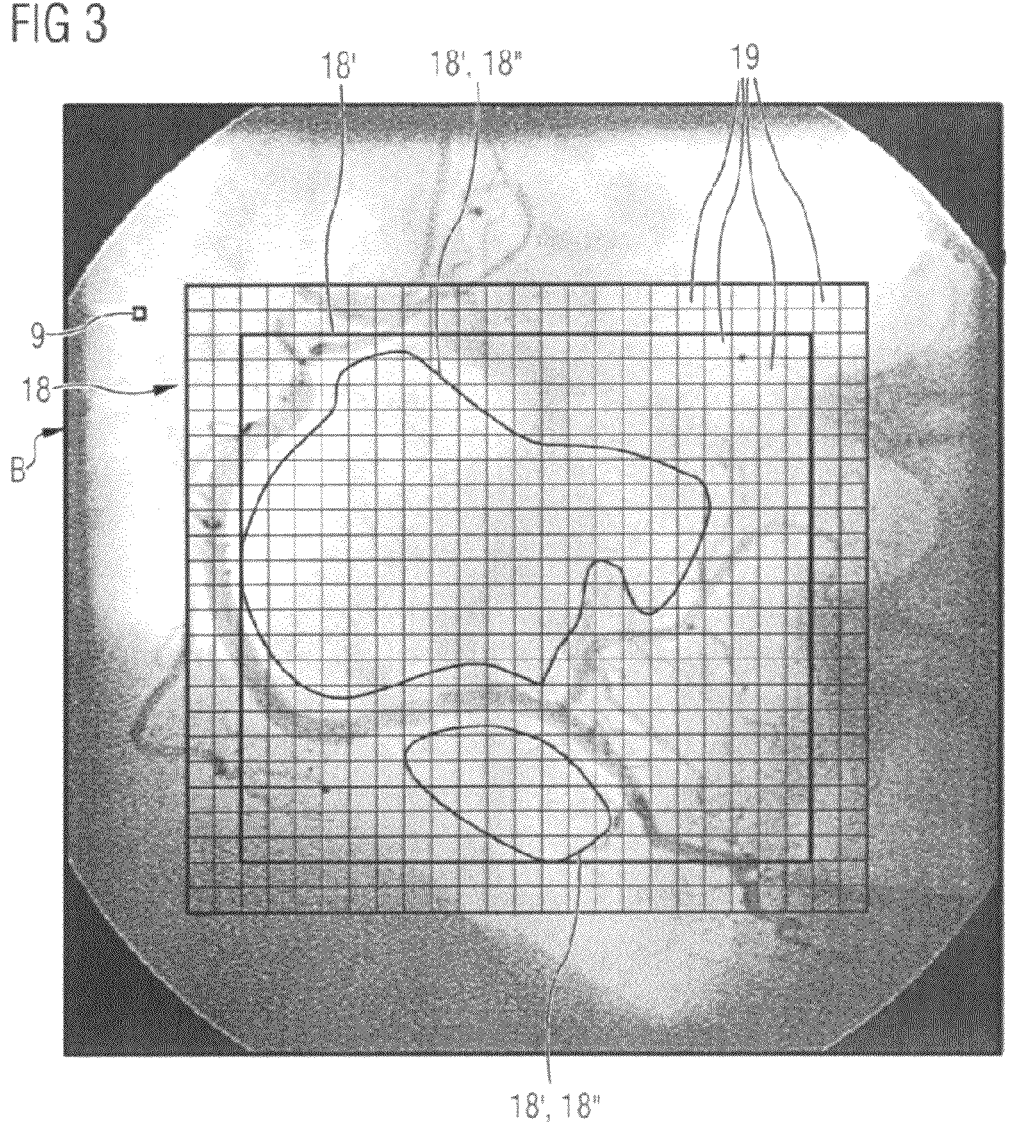
FIG. 3 shows an example of a projection image.

FIG. 3 shows one of the captured images B by way of example. It can be seen from FIG. 3 that the image B is two-dimensional and contains a plurality of pixels 9. The resolution of the image B is even so high that the individual pixels 9 are no longer recognizable in the image B shown. Purely by way of example, one of the pixels 9 is marked with the reference numeral 9. Each pixel 9 has a pixel value which lies e.g. between 0 and 255 ($=2^8-1$).

It can also be seen from FIG. 3 that the examination subject 3 contains a vascular system and its surroundings. Due to the fact that the images B in their entirety form a time sequence, the images B also show the variation over time of the distribution of the contrast medium in the examination subject 3.

If the examination subject 3 remained motionless during the capturing of the images B (for example because images B of the brain of the person 3 were recorded) or if, due to an appropriate triggering of the recording (for example, always 0.6 seconds after the R-wave of the ECG), the images B always show the examination subject 3 in the same phase position, the image capturing as such already guarantees that the pixel values of pixels 9 corresponding to one another in the images B are defined by at least essentially locally identical areas of the examination subject 3. In this case all the captured images B can be defined as projection images B within the meaning of the comments that follow. Otherwise, a suitable selection must be made. This is explained in detail below in conjunction with FIGS. 4 and 5.

Figure 4:
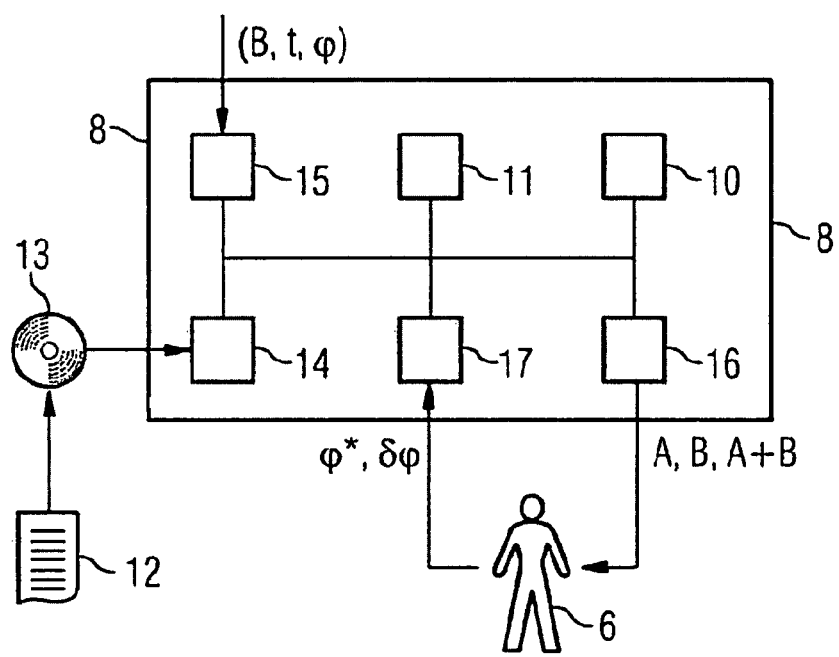
FIG. 4 shows a block diagram of an evaluation device.

Referring to FIG. 4, the evaluation device 8—which can in principle be identical with the control device 2—comprises inter alia an arithmetic logic unit 10 and a mass storage means 11. A computer program 12 is stored in the mass storage means 11. When the computer program 12 is invoked, the evaluation device 8 executes a representation method which is described in detail below. The evaluation device 8 constitutes a computer within the meaning of the present invention. It should, however, also be mentioned beforehand that the computer program 12 must previously have been supplied to the evaluation device 8. The program can be supplied, for example, by means of a suitable data medium 13 on which the computer program 12 is also stored. Said data medium 13 is introduced into a suitable interface 14 of the evaluation device 8 so that the computer program 12 stored on the data medium 13 can be read out and stored in the mass storage means 11 of the evaluation device 8.

Figure 5:
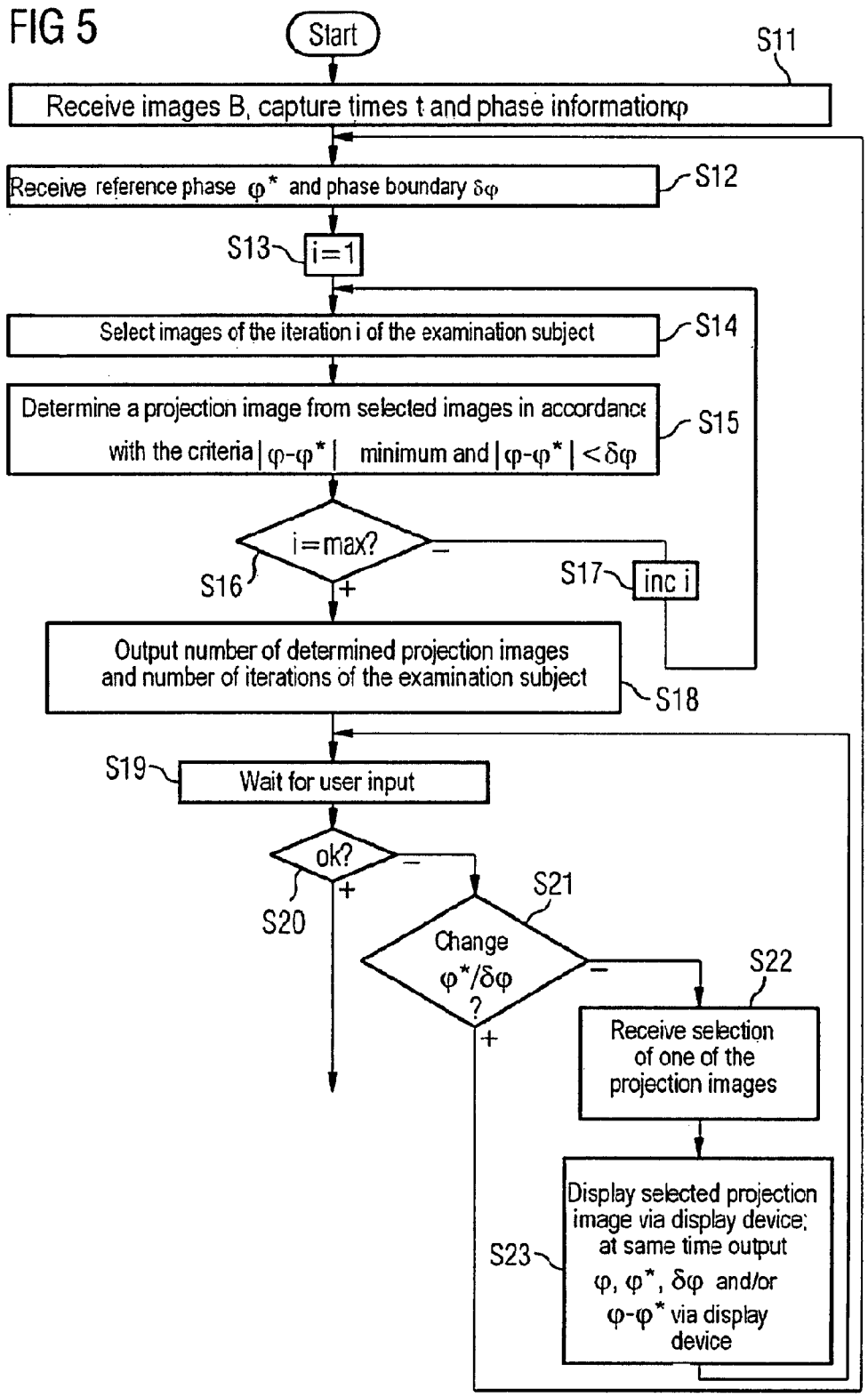
FIGS. 5 and 6 are flowcharts.

Referring to FIG. 5, in a step S11 the images B themselves are supplied to the evaluation device 8 via an appropriate interface 15. The same applies to the corresponding capture times t and the assigned phase information $\phi$. In order to select the projection images B from the captured series of images B, the appropriate selection criteria $\phi^*$, $\delta\phi$ must also be known to the evaluation device 8, namely a reference phase position $\phi^*$ and a phase boundary $\delta\phi$. It is possible in this case that the reference phase $\phi^*$ and the phase boundary $\delta\phi$ are stored within the evaluation device 8. According to FIG. 5, the reference phase $\phi^*$ and the phase boundary $\delta\phi$ are preferably specified for the evaluation device 8 in a step S12 by the user 6 via an appropriate input device 17. For example, it is possible for the user 6, by means of appropriate inputs, to scroll through the captured sequence of images B and to select one of the images B. The phase information $\phi$ of the image B selected in this way defines the reference phase $\phi^*$, and the distance from the immediately succeeding and immediately preceding image B defines the phase boundary $\delta\phi$. It is also possible for the user 6 to specify the appropriate values $\phi^*$, $\delta\phi$ explicitly by means of numerical values. Finally, it is possible for the computer 8 to output the ECG signal to the user 6 via a display device 16 and for the user 6 to set appropriate markers in the ECG signal. In all cases the user 6 can specify the values $\phi^*$ and $\delta\phi$ alternatively as absolute time values or as relative phase values.

In steps S13 to S17, the actual selection of the projection images B from the entire series of images B is made. Toward that end, firstly in a step S13 an index i is set to the value one. In step S14, the evaluation device 8 then selects the images B of the iteration i of the examination subject 3. Within the images B now selected, the evaluation device 8 generally defines one (in exceptional cases also none) of the images B as a projection image B, for it looks in step S15 firstly for the particular image among the selected images B in which the size of the difference of the phase information $\phi$ relative to the reference phase $\phi^*$ is at a minimum. It then checks whether this difference is less than the phase boundary $\delta\phi$. If the evaluation device 8 can determine such an image B, it defines this image B in step S115 as the projection image B for the respective iteration i. If it cannot determine any such image B, it notes this accordingly.

In step S16, the evaluation device 8 checks whether the index i has already reached its maximum value. If this is not the case, the evaluation device 8 increments the index in step S17 and goes back to step S14. Otherwise, the definition of the projection images B is complete.

By means of this (purely exemplary) procedure it is ensured that the pixel values of pixels 9 corresponding to one another in the projection images B are also defined by at least essentially locally identical areas of the examination object 3 when the examination subject 3 has moved iteratively during the capturing of the entire series of images B.

In a step S18, the evaluation device 8 outputs the number of projection images B determined and the number of iterations of the examination subject 3 to the user 6 via the display device 16. The user can thus recognize whether he/she has made a good choice in respect of the reference phase $\phi^*$ and/or the phase boundary $\delta\phi$. In a step S19, the evaluation device 8 waits for a user input. When such an input has been made, the evaluation device 8 checks in a step S20 whether this input was a confirmation by the user 6. If this is the case, the selection of projection images B is complete and the process can continue with the actual presentation method.

Otherwise the evaluation device 8 checks in a step S21 whether the user 6 has input a request for the reference phase $\phi^*$ and/or the phase boundary $\delta\phi$ to be changed. If this is the case, the evaluation device 8 goes back to step S12.

Otherwise the user 6 has input a request for one of the projection images B to be displayed. In this case the evaluation device 8 receives a corresponding selection from the user 6 in a step S22. In a step S23, it displays the selected projection image B on the display device 16. Together with the selected projection image B it also outputs the corresponding phase information $\phi$ of the selected projection image B, the reference phase $\phi^*$, their difference and the phase boundary $\delta\phi$ to the user 6 via the display device 16. It then goes back to step S19. Where desirable it would also be possible to display an overall representation of the phase curve and to display the phase information $\phi$ of all the projection images B simultaneously.

It should be mentioned for the sake of completeness that steps S12 to S23 are appropriate and/or necessary only when a selection of the projection images B has to be made from the entire series of images B. If, on the other hand, the captured images B are all suitable a priori, steps S12 to S23 can be omitted.

It should also be mentioned that as an alternative to the procedure described above in conjunction with FIG. 5, it is also possible to specify in advance suitable intervals for the phase information $\phi$ and to determine for each interval the number of possible projection images B. The evaluation device 8 can in this case output a list or table with the aid of which the user 6 can recognize how many projection images B are available to him/her and for which phase interval in each case. In this case the user 6 has merely to select the phase interval desired by him/her.

Figure 6:
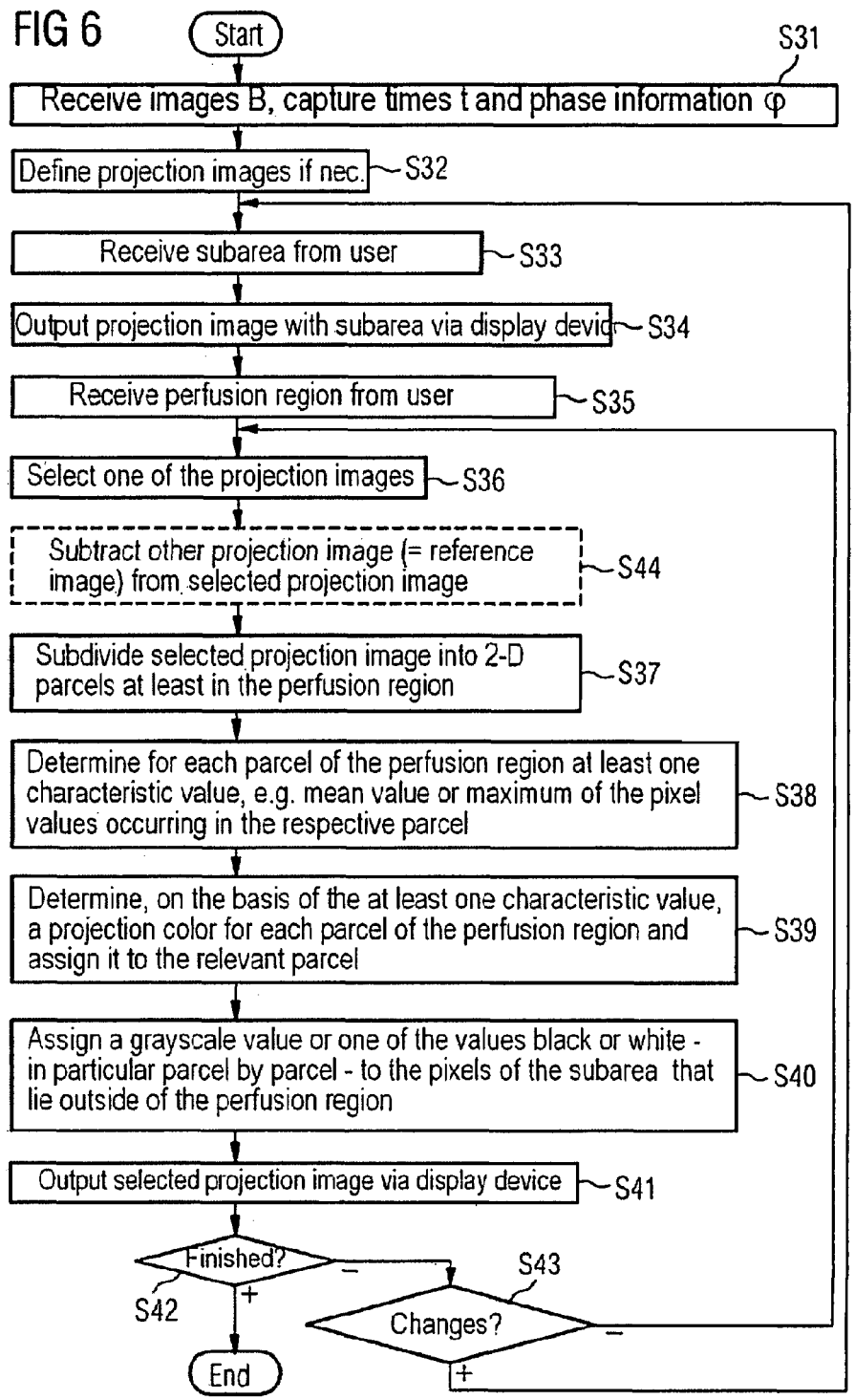

When the selection of projection images B from the entire series of images B has been completed, the process continues with FIG. 6. Steps S31 and S32 in FIG. 6 correspond on the one hand to step S11 and on the other to steps S12 to S23 in FIG. 5. Since step S32 is, as previously mentioned, only optional, it is represented in FIG. 6 by dashed lines only.

In a step S33, the evaluation device 8 receives a subarea 18 from the user 6. In a step S34, the evaluation device 8 inserts this subarea 18 into one of the projection images B and outputs this projection image B together with the marker of the subarea 18 to the user 6 via the display device 16. This can also be seen from FIG. 3. The subarea 18 corresponds to the black frame in FIG. 3.

In a step S35, a perfusion region 18' is specified to the computer 8 by the user 6. The perfusion region 18' can for example be drawn by the user 6 into the projection image B output via the display device 16 in step S34. The perfusion region 18' can be inherently contiguous. Alternatively it can also comprise a plurality of subareas 18" separated from one another. Possible projection regions 18' and subareas 18" are drawn in FIG. 3.

In a step S36, the computer 8 selects one of the projection images B. For example, the computer 8 can receive a corresponding input from the user 6. Other approaches in which the computer 8 automatically determines the projection image B are conceivable.

In a step S37, the computer 8 subdivides the projection image B selected in step S36 into two-dimensional parcels 19. The subdivision into parcels 19 can, as shown in FIG. 3, be performed over the entire subarea 18. It can also be performed in the entire projection image B. It is always performed at least in the projection region 18'.

The subdivision of the parcels 19 can be seen, for example, from FIG. 3. According to FIG. 3, the parcels 19 are rectangular. This is the simplest type of subdivision into parcels 19. Other parcel forms are also possible, in particular equilateral triangles and regular hexagons.

The size of the parcels 19 is freely selectable, though they must be two-dimensional. Furthermore they should comprise sufficiently many pixels 9 that when a mean value is formed the noise tends to be averaged out and motion artifacts are at least generally negligible. On the other hand the resolution should be sufficiently good. It has been established in trials that the parcels should preferably contain between about 60 and around 1000 pixels, which in the case of rectangular parcels 19 can correspond to an edge length of e.g. 8×8 pixels to e.g. 32×32 pixels.

In a step S38, the computer 8 determines at least one characteristic value C for each parcel 19 of the perfusion region 18'. For example, the computer 8 can determine the maximum and/or the mean value of the pixel values occurring in the respective parcel 19 as a characteristic value C for each parcel 19.

In the course of step S38, the computer 8 can also, where necessary, additionally determine the at least one characteristic value C outside of the perfusion region 18'. This is not, however, absolutely essential within the context of FIG. 6.

In a step S39, the computer 8 determines for each parcel 19 of the perfusion region 18' a color PF with the aid of the at least one characteristic value C and assigns it to the respective parcel 19. The color PF is referred to below as the projection color PF in order to distinguish it from other colors.

Figure 7:
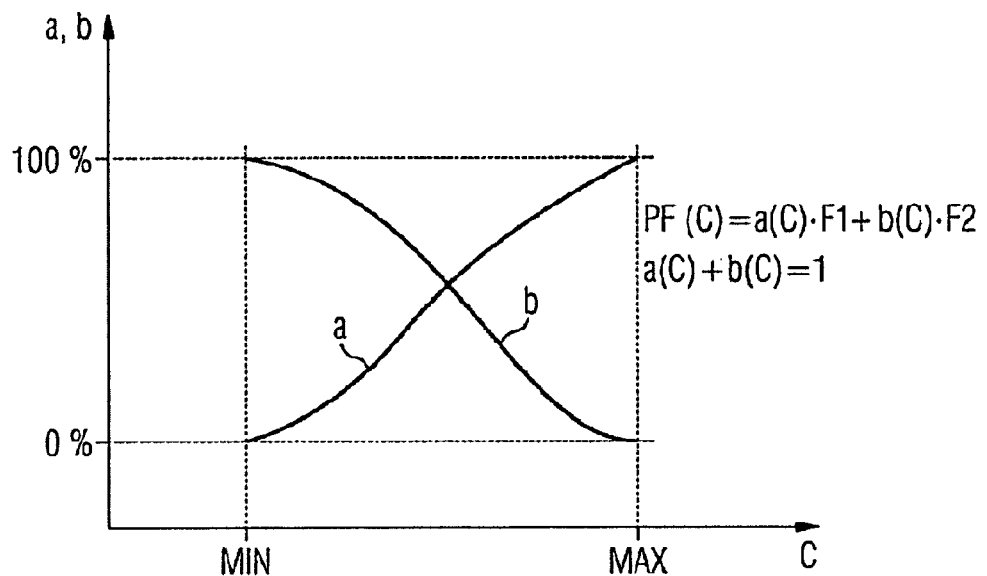
FIGS. 7 and 8 show possible color assignments.
Figure 8:
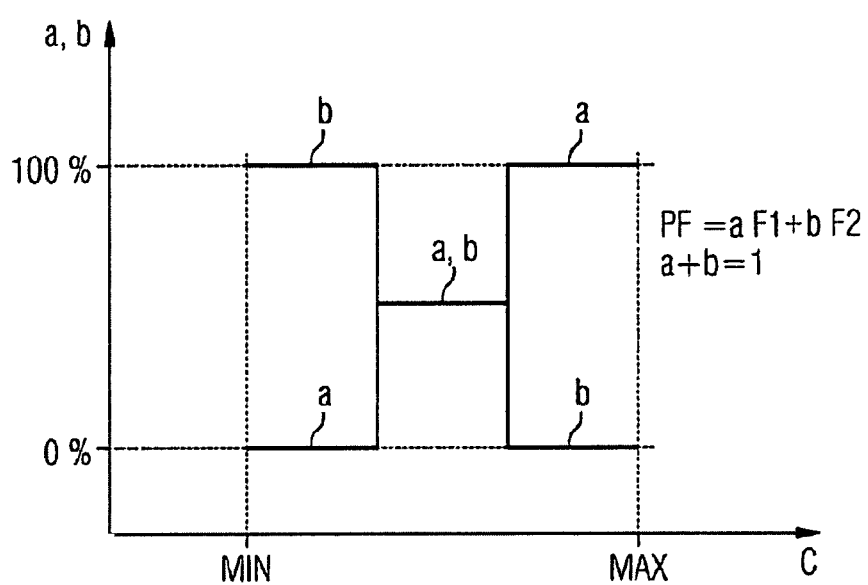

Referring to FIGS. 7 and 8, the at least one characteristic value C lies between a minimum value MIN and a maximum value MAX. As can be seen from FIGS. 7 and 8, the projection color PF consists in a first proportion a of a first color F1 and in a second proportion b of a second color F2. The first proportion a and the second proportion b are monotonous functions of the characteristic value C. For a specific characteristic value C they always mutually complement each other to 100%.

The first and the second color F1, F2 can in principle be any colors F1, F2. Preferably the colors F1, F2 are primary colors within the meaning of the color circle, in other words two of the colors yellow, red and blue. Yellow and red in particular have proven a good choice in trials.

The assignment of the first and second proportion a, b to a specific characteristic value C can—see FIG. 7—increase or decrease continuously with the characteristic value C. Alternatively it can—see FIG. 8—be constant in sections. Hybrid forms are also possible.

It is possible to perform step S38 over the entire subarea 18, in other words also outside of the perfusion region 18'. Preferably the color assignment takes place only within the perfusion region 18'. In this case the computer 8 assigns, preferably in a step S40, a grayscale value or one of the values black or white to the pixels 9 lying outside of the perfusion region 18'.

If the pixels 9 are assigned a grayscale value, the assignment can be performed pixel by pixel. In particular the actual pixel value of the respective pixel 9 of the selected projection image B can be used as a grayscale value. Alternatively it is possible for example also to subdivide the subarea 18 outside of the perfusion region 18' into parcels 19 and to assign a characteristic value C to each parcel 19 (compare steps S37 and S38). The grayscale value can in this case be determined by the characteristic value C. On the other hand a color assignment according to step S39 should not take place.

If it is known whether a specific pixel 9 (or, as the case may be, a specific parcel 19) is vessel or background, it is furthermore possible to assign a first grayscale value to pixels 9 (parcels 19) of type vessel, and a second grayscale value to pixels 9 (parcels 19) of type background. In the extreme case each one of the two last-mentioned grayscale values can be the minimum and maximum of the grayscale values possible in principle. In this case an assignment of the colors black and white results.

Figure 9:
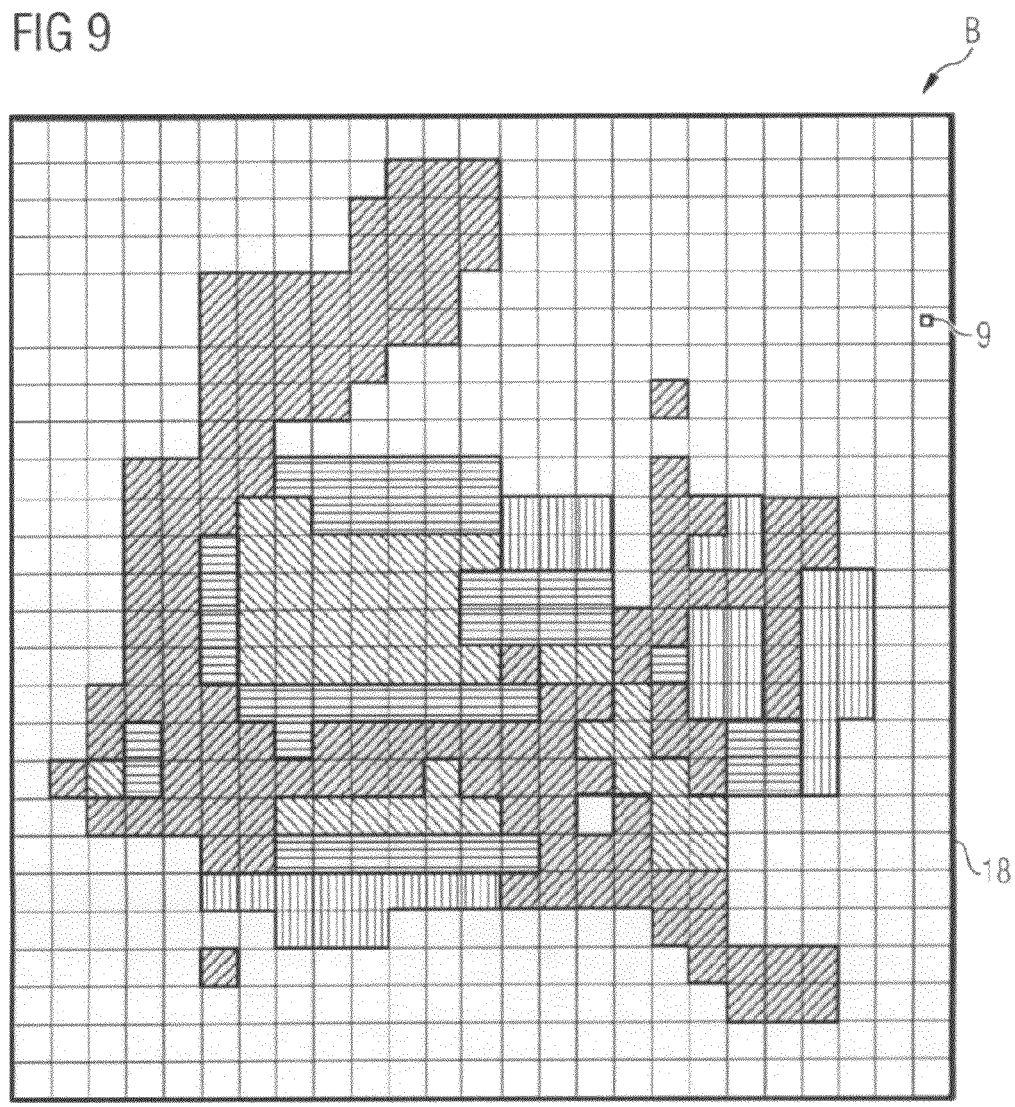
FIG. 9 shows a possible representation of a projection image.

In a step S41, the computer 8 outputs the projection image B selected in step S36 (or at least its subarea 18) to the user 6 via the display device 16. The computer 8 represents the parcels 19 of the perfusion region 18 in their assigned projection color PF. The computer 8 displays the remaining pixels 9 (or parcels 19) either in color or (preferably) in a grayscale or black/white representation. FIG. 9 shows a possible representation of the selected projection image B.

In a step S42, the computer 8 prompts the user 6 to confirm whether the method of FIG. 6 is to be terminated. If the method of FIG. 6 is not to be terminated, the computer 8 goes to a step S43. In step S43, the computer 8 checks whether the subarea 18 and/or the perfusion region 18' is to be changed. Depending on the result of the check, the computer 8 returns to step S33 or to step S36.

It is possible for the computer 8, prior to determining the at least one characteristic value C, to subtract another projection image B (referred to below as reference image B) from the selected projection image B. This is indicated in FIG. 6 by means of a step S44. Step S44 is only optional, however, and is therefore represented in FIG. 6 by dashed lines only.

Any projection image B is suitable in principle for use as a reference image B within the meaning of step S44. For example, the chronologically first projection image B can be used. A separate reference image B can also be used for each projection image B.

Figure 10:
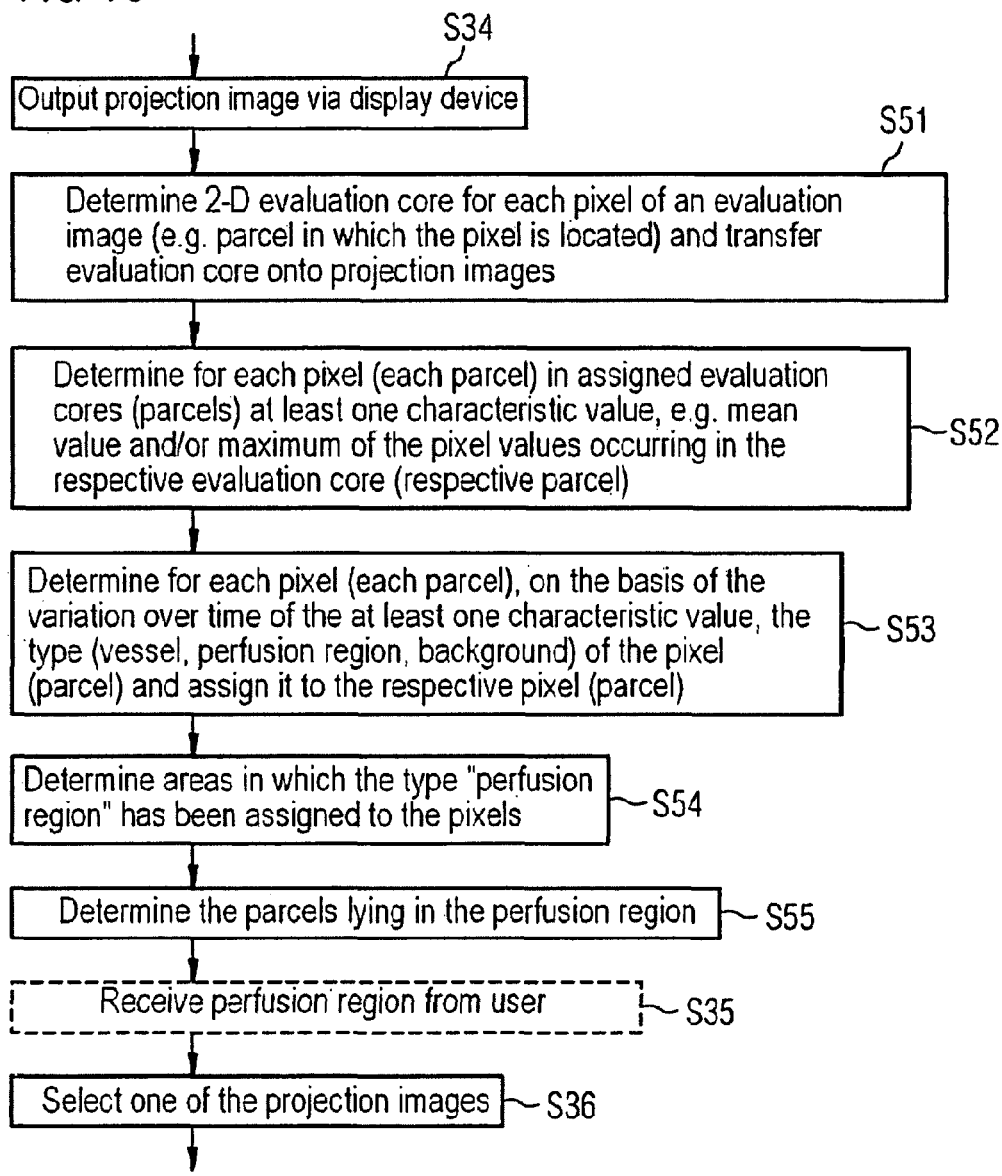
FIGS. 10 to 12 are flowcharts.

Within the context of FIG. 6, in step S35 the perfusion region 18' is specified by the user 6. Referring to FIG. 10, it is possible to replace or supplement step S35 with a determination of the perfusion region 18. This determination or, as the case may be, supplementing is performed automatically by the computer 8.

Referring to FIG. 10, it is possible to insert steps S51 to S55 between steps S34 and S36 (if step S35 is replaced) or between steps S34 and S35 (if step S35 is supplemented).

In step S51, the computer 8 determines, for each pixel 9 of an evaluation image A, a two-dimensional evaluation core 19 specific to the respective pixel 9. The computer 8 transfers said evaluation core 19 onto the projection images B.

The two-dimensional evaluation core 19 can be for example a pixel group of predefined size around the respective pixel 9. In the simplest case the evaluation core 19 corresponds to the parcels 19 of the subarea 18. In this case the computer 8 defines the parcel 19, in which the relevant pixel 9 lies, as the evaluation core 19 for each pixel 9 of the evaluation image A. Irrespective of the actual determination of the evaluation core 19, however, the evaluation core 19 is uniform for all projection images B.

In step S52, the computer 8 determines at least one characteristic value (for example the mean value and/or the maximum of the pixel values occurring in the respective evaluation core 19) in each case for each pixel 9 in the assigned evaluation cores 19 of the projection images B.

Based on the variation over time of the at least one characteristic value, the computer 8 determines in step S53 whether the relevant pixel 9 belongs to a vessel of the vascular system, to the background or to the perfusion region 18'. Similarly in step S53, the computer 8 assigns the relevant type to the respective pixel 9 of the evaluation image A.

The computer 8 can, for example, assign the type "background" to a pixel 9 of the evaluation image A if the characteristic value varies only slightly. Depending on whether there is a significant increase in the characteristic value before or after a threshold time, the computer 8 can assign one of the types "vessel" or "perfusion region" to the pixels 9 that have not been assigned the type "background" by the computer 8. Corresponding possible approaches are described in detail in DE 10 2005 039 189.3; see FIGS. 11 to 13 in that document in conjunction with the description pages 30 and 31 therein. Further possible approaches can be found in the German patent application "Image evaluation method for two-dimensional projection images and objects corresponding thereto", filed simultaneously with the present invention, of Siemens AG, bearing the Siemens internal reference no. 200601059.

It is possible, as already mentioned, for the parcels 19 to be used as evaluation cores 19. In this case the type assignment of step S53 can be performed parcel by parcel. If the type is assigned parcel by parcel, steps S54 and S55 can be omitted.

If steps S54 and S55 are present, in step S54 the computer 8 determines the areas 18', 18" in which it has assigned the type "perfusion region" to the pixels 9. In step S55, it defines the parcels 19 on the basis of the perfusion region 18' determined in step S54. For example, in step S55 the computer 8 can define a suitable subdivision of the perfusion region 18' into the parcels 19. In so far as is necessary, the computer 8 can optionally adjust the size and/or the shape of the parcels 19 accordingly for this purpose.

The representation method described hereintofore already works very well. It can be improved by means of the embodiments described in the following.

A first possible embodiment is explained in more detail below in conjunction with FIG. 11.

Figure 11:
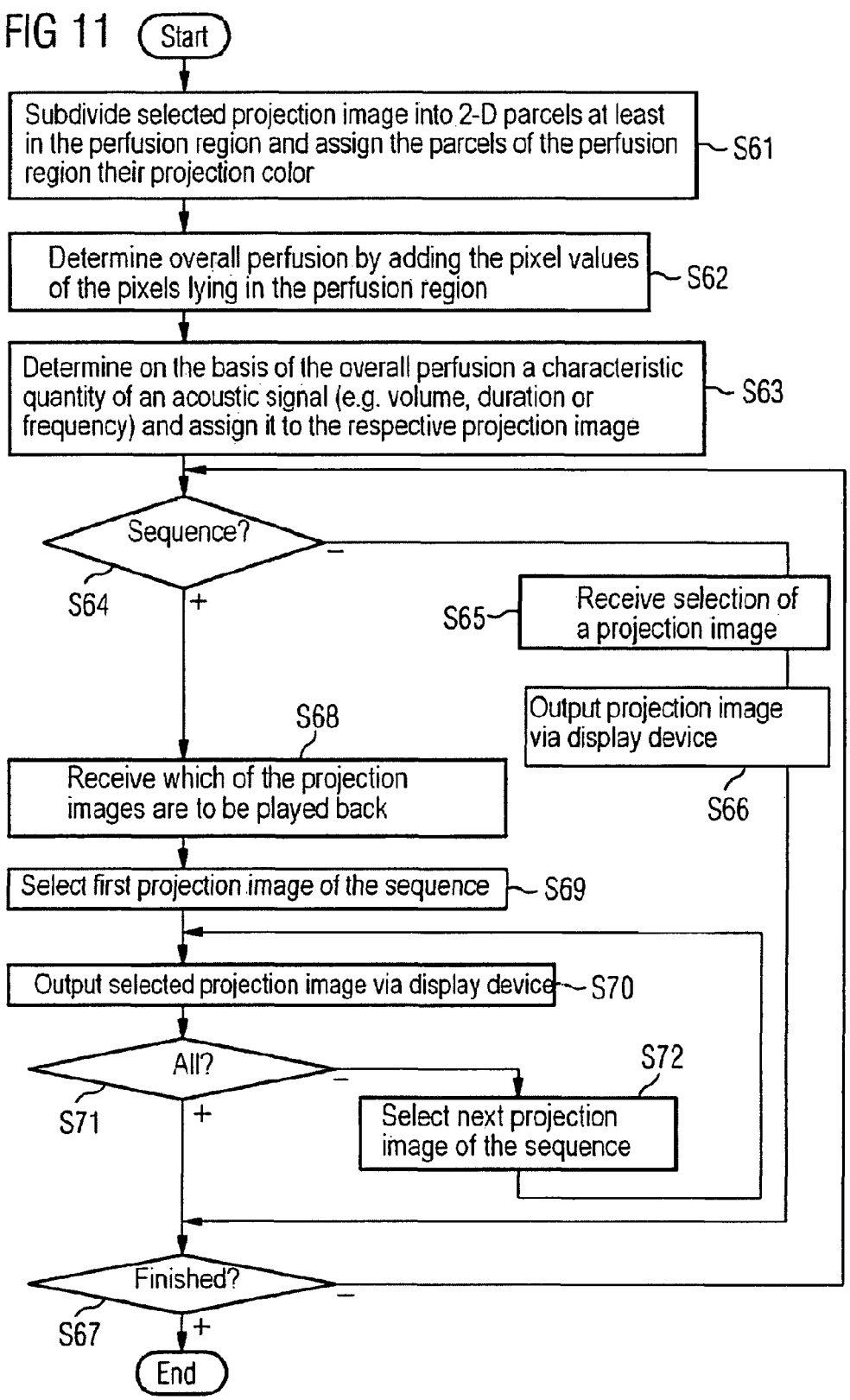

Referring to FIG. 11, in a step S61 the computer 8 subdivides the projection images B into parcels 19. The parcels 19 are uniform for all projection images B. The subdivision can alternatively be performed either only inside the perfusion region 18' or inside and outside the perfusion region 18'. In addition the computer 8 assigns the associated perfusion colors PF to the parcels 19 of the projection images B that lie in the perfusion region 18'. Step S61 thus corresponds in essence to the procedure of steps S37 to S40 (possibly including step S44) described above in connection with FIG. 6.

In a step S62, the computer 8 determines an overall perfusion G for each projection image B. For this purpose it adds up the pixel values of the pixels 9 lying in the perfusion region 18' (or, if step S44 is present, the differences of the pixel values of the pixels 9 of the respective projection image B from the pixel values of the corresponding pixels 9 of the reference image B).

In a step S63, the computer 8 defines a characteristic quantity of an acoustic signal, for example the volume, the duration or the frequency of the acoustic signal, on the basis of the overall perfusion G. It assigns said characteristic quantity to the relevant projection image B.

Where appropriate, the now established sequence of color-coded projection images B can be stored. This is not shown in the figures.

In a step S64, the computer 8 checks whether a command to play back the sequence of projection images B has been specified to it by the user 6. If the command to play back the sequence of projection images B has not been specified to the computer 8, it goes to a step S65. In step S65, a single image is output. For this purpose the computer 8 receives an instruction from the user 6 specifying which of the projection images B it is to output via the display device 16. The computer 8 outputs this projection image B in a step S66. In the course of step S66, the computer 8 can, where necessary, additionally output the acoustic signal via a loudspeaker 20 (compare FIG. 4) in parallel with the optical output of the projection image B.

In a step S67, the computer 8 prompts the user 6 to confirm whether the routine of FIG. 11 is to be terminated. If it is not to be terminated, the computer 8 returns to step S64.

If the computer 8 does not proceed to step S65 from step S64, it goes to a step S68. In step S68, the computer 8 receives an instruction from the user 6 specifying which of the projection images B it is to play back as a sequence.

Step S68 is only optional. If it is not present, the sequence is predefined as a fixed sequence. For example the projection images B can always be played back starting with the first, second or third projection image B until the sequence has been displayed in full.

In a step S69, the computer 8 selects the chronologically first projection image B of the sequence of projection images B that is to be displayed. In a step S70, the computer 8 outputs the selected projection image B to the user 6 via the display device 16. At the same time, in the course of step S70, it can additionally output the acoustic signal.

In a step S71, the computer 8 checks whether it has already displayed the sequence of projection images B in full. If this is not the case, it proceeds to a step S72 in which it selects the next projection image B in chronological order. It then returns to step S70.

If the computer 8 has displayed the sequence in full, it proceeds from step S71 to step S67.

The procedure shown in FIG. 11 (in particular steps S69 to S72) is advantageous in particular because the user 6 can on the one hand observe a color-coded representation of the distribution of the perfusion in the respective projection image B and at the same time easily recognize the overall perfusion G with the aid of the acoustic signal modulated in accordance with the characteristic quantity. The procedure of FIG. 11 is even optimal if the sequence is displayed in real-time, in other words the succession of the projection images B corresponds to the time interval of their capture times $t_i$.

Figure 12:
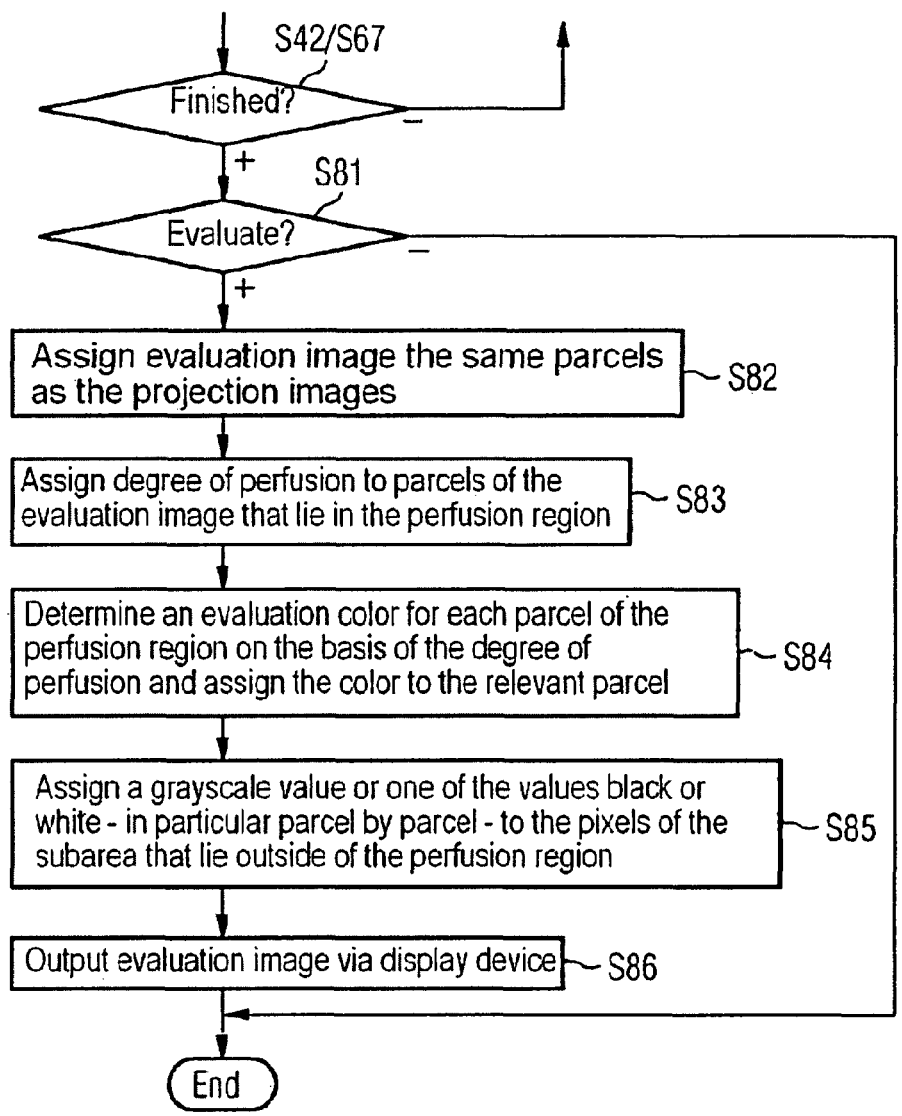

The procedure shown in FIGS. 6 and 11 can furthermore be additionally improved by the procedure shown in FIG. 12.

Referring to FIG. 12, steps S81 to S86 can follow on from step S42 of FIG. 6 or, as the case may be, step S67 of FIG. 11. In step S81, the computer 8 checks whether a computer-aided determination of the degree of perfusion of the parcels 19 of the perfusion region 18 is to be performed. Only if this is the case does the computer 8 perform steps S82 to S86.

In step S82, the computer 8 assigns the same parcels 19 to the evaluation image A as to the projection images B. If the perfusion region 18 was determined by the computer 8 (compare FIG. 10), the subdivision into parcels performed there can be taken over.

In step S83, the computer 8 assigns a degree of perfusion to the parcels 19 of the evaluation image A that lie in the perfusion region 18'. For example, the computer 8 can determine the degree of perfusion on the basis of the time position of the maximum of the characteristic value C and the period of time during which the characteristic value C exceeds a predefined threshold value and assign it to the relevant parcel 19.

In step S84, the computer 8 determines a color AF for each parcel 19 of the perfusion region 18' and assigns it to the relevant parcel 19. The color AF is referred in the following as evaluation color AF in order to distinguish it from other colors (in particular from the projection color PF).

The evaluation color AF is preferably determined analogously to the manner in which the projection color PF is determined. In particular the evaluation color AF assigned to the maximum possible degree of perfusion should correspond to the projection color PF assigned to the maximum possible characteristic value C. Also, the evaluation color AF assigned to the minimum possible degree of perfusion should preferably correspond to the projection color PF assigned to the minimum possible characteristic value C.

Analogously to the projection images B, the evaluation image A can also be color-coded outside of the perfusion region 18'. Preferably—likewise analogously to the projection images B—it is represented in grayscale values or only in black/white outside of the perfusion region 18'. In step S85, in particular a first grayscale value can be assigned to the pixels 9 of type "vessel", and a second grayscale value to the pixels 9 of type "background". In the extreme case the grayscale values can assume the values black and white. If the evaluation image A is also subdivided into parcels 19 outside of the perfusion region 18', the assignment of the grayscale values in step S85 can take place parcel by parcel.

Figure 13:
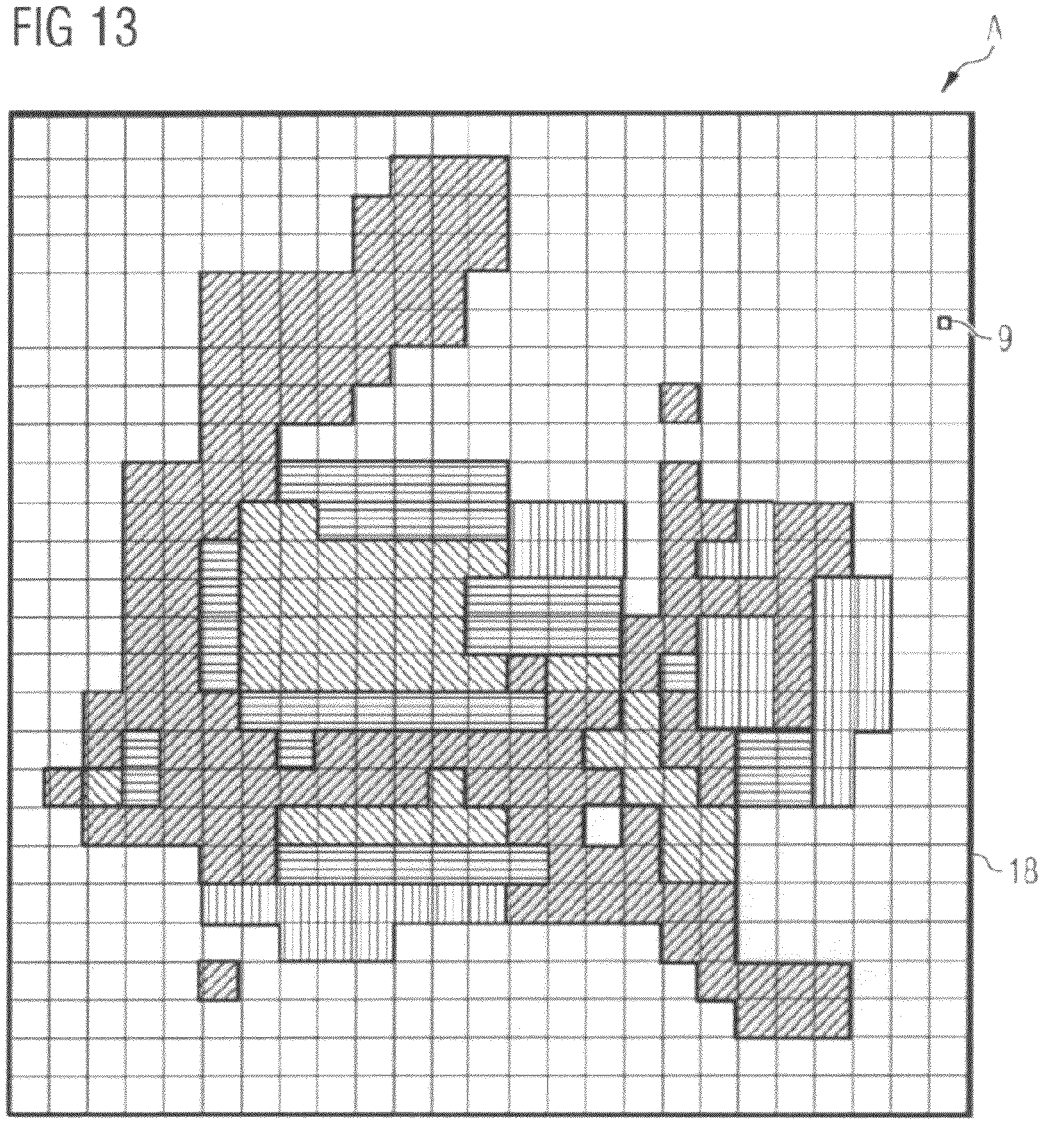
FIG. 13 shows an evaluation image.

In step S86, the computer 8 outputs the evaluation image A to the user 6 via the display device 16, representing each parcel 19 of the perfusion region 18' of the evaluation image A in its assigned evaluation color AF. The computer 8 represents the remaining pixels 9—where necessary parcel by parcel—either also in color or (preferably) in grayscales or in black/white. FIG. 13 shows a possible representation of the evaluation image A.

The representation shown in FIG. 13 corresponds to the representation shown in FIG. 9. The correspondence between FIG. 9 and FIG. 13 is only accidental, however. As a rule the representations are different from one another.

Figure 14:
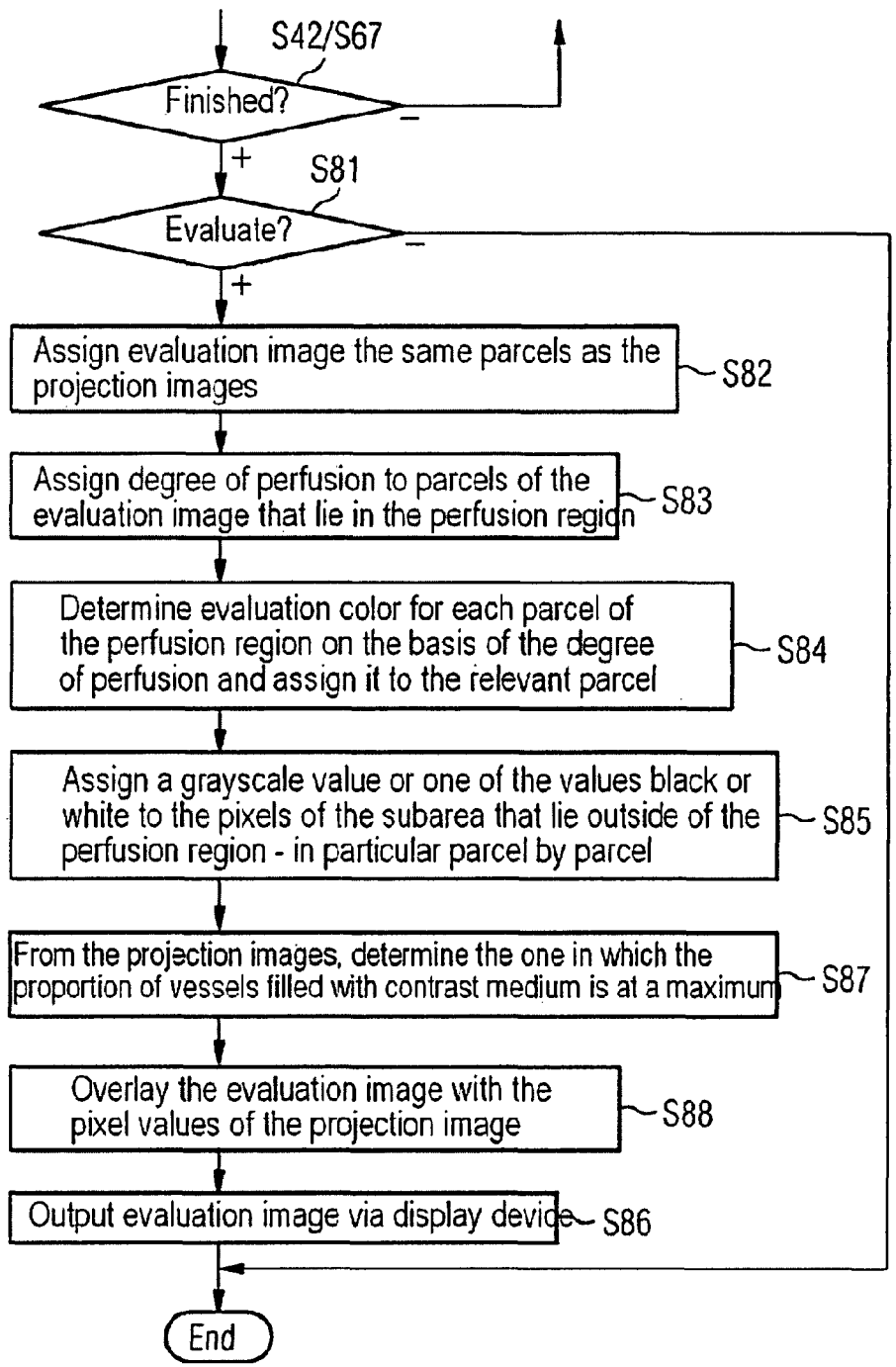
FIG. 14 is a flowchart and FIG. 15 shows an overlay image.
Figure 15:
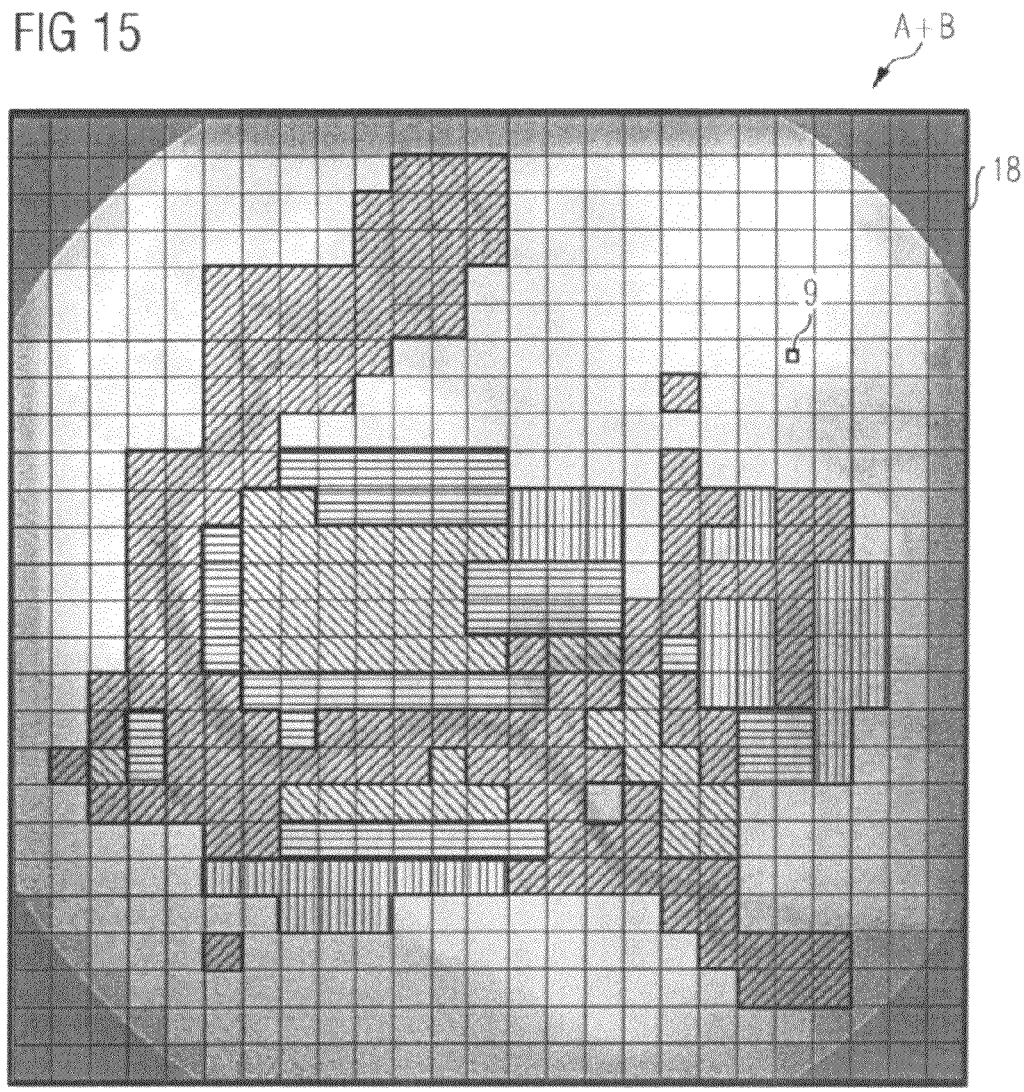

The procedure shown in FIGS. 12 and 13 can be varied in accordance with FIGS. 14 and 15.

The procedure shown in FIG. 14 corresponds in its approach to the procedure shown in FIG. 12. Steps S87 and S88 are present in addition in FIG. 14, however. Step S88 is mandatory (in the context of FIG. 14). Step S87 is optional.

In step S87, the computer 8 determines that image from the projection images B in which the proportion of vessels filled with contrast medium is at a maximum. For example, the computer 8 can for this purpose determine the type for all pixels 9 of the projection images B and select that image from the projection images B in which the number of pixels 9 of type "vessel" whose pixel value lies above a predefined bound is at a maximum. Other approaches are also possible.

If step S87 is omitted, the projection image B can—as a substitute for the omitted step S87—be permanently predefined (e.g. the third projection image B is always used) or the selection of the projection image B can be specified to the computer 8 by the user 6. It is also possible for the computer 8 to determine the vascular system as a whole on the basis of the projection images B and thus generate an additional "projection image" B which will be used in the course of step S88.

In step S88, the computer 8 overlays the evaluation image A with the pixel values of the projection image B determined in step S87. FIG. 15 shows an example of the overlay image produced in this way.

The representation method according to the invention has a high degree of automation and a high processing speed. Furthermore it is very flexible, including in the context of the visualization of the evaluation result and in the context of interactivity. Finally it is also possible to integrate the representation method according to the invention into the framework of what is referred to as a TIMI flow measurement. In this way a duplicated capturing of the projection images B in conjunction with the associated X-ray load on the patient 3 can be avoided.

The above description serves solely to explain the present invention. The scope of protection of the present invention, on the other hand, is to be determined exclusively by the appended claims.

The invention claimed is:

1. A method for representing two-dimensional projection images of an examination object showing a variation of a distribution of a contrast medium over time in the examination object, comprising:
    subdividing a two-dimensional project image that is to be displayed from the two-dimensional projection images into a grid pattern having a plurality of parcels in a perfusion region of the examination object, wherein each of the parcels has a predetermined shape and each parcel includes a plurality of pixels;
    determining a characteristic value for each parcel in the perfusion region;
    determining a projection color for the each parcel based on the characteristic value;
    assigning the projection color to the each parcel;
    outputting a subarea of the two-dimensional projection image comprising the perfusion region with the each parcel in the perfusion region being represented by the assigned projection color;
    providing a computer for performing said steps of subdividing a two-dimensional project image, determining a characteristic value, determining a projection color, assigning the projection color and outputting a subarea of the two-dimensional projection image; and
    recording the two-dimensional projection images on an image recording device.

2. The method as claimed in claim 1, wherein the examination object comprises a vascular system and surroundings of the vascular system.

3. The method as claimed in claim 1,
    wherein the characteristic value is determined based on pixel values occurring in the each parcel of the two-dimensional projection image or differences of pixel values of the each parcel between the two-dimensional projection image and another two-dimensional projection image from the two-dimensional projection images, and
    wherein the pixel values are determined by at least essentially locally identical areas of the examination object.

4. The method as claimed in claim 1, wherein a portion of the two-dimensional projection image outside the perfusion region is represented in black/white or as a grayscale image.

5. The method as claimed in claim 4, wherein the portion of the two-dimensional project image is subdivided into a further plurality of parcels and each of the further parcels is assigned a grayscale value or a black/white value.

6. The method as claimed in claim 1, wherein the perfusion region is specified by a user or automatically determined by a computer.

7. The method as claimed in claim 1,
    wherein an evaluation core of the two-dimensional projection image is determined by a pixel and is identical for all the two-dimensional projection images, and
    wherein whether the pixel belongs to the perfusion region is determined based on a variation over time of pixel values of the pixel in the evaluation core.

8. The method as claimed in claim 7, wherein the evaluation core corresponds to one of the parcels comprising the pixel.

9. The method as claimed in claim 1,
    wherein an overall perfusion is determined by adding up:
        pixel values of each pixel in the perfusion region of the two-dimensional projection image, or
        differences of pixel values of the each pixel in the perfusion region between the two-dimensional projection image and another two-dimensional projection image from the two-dimensional projection images, and
    wherein an acoustic signal is determined based on the overall perfusion and outputted.

10. The method as claimed in claim 1, wherein the characteristic value is between a minimum value and a maximum value.

11. The method as claimed in claim 1,
    wherein the projection color comprises a first proportion of a first color and a second proportion of a second color,
    wherein the first proportion is a monotonous function of the characteristic value, and
    wherein the first and the second colors are primary colors.

12. The method as claimed in claim 1, wherein the two-dimensional projection images are recorded in a chronological sequence and outputted one after the other according to the chronological sequence.

13. The method as claimed in claim 1, further comprising:
    subdividing an evaluation image corresponding to the two-dimensional projection image into a plurality of parcels in the perfusion region,
    determining a degree of perfusion for each parcel in the perfusion region of the evaluation image,
    assigning an evaluation color to the each parcel based on the degree of perfusion, and
    outputting a subarea of the evaluation image comprising the perfusion region with the each parcel in the perfusion region being represented by the assigned evaluation color.

14. The method as claimed in claim 13, wherein a portion of the evaluation image outside the perfusion region is represented in black/white or as a grayscale image.

15. The method as claimed in claim 14, wherein the portion of the evaluation image is subdivided into a further plurality of parcels and each of the further parcels is assigned a grayscale value or a black/white value.

16. The method as claimed in claim 13, wherein a two-dimensional projection image having a proportion of vessels of the examination object that is maximally filled with the contrast medium is automatically determined from the two-dimensional projection images and is overlaid onto the evaluation image.

17. A computer program loadable to a computer for performing a representation method for two-dimensional projection images of an examination object showing a variation of a distribution of a contrast medium over time in the examination object, comprising:

a computer subroutine that is stored on a non-transitory computer-readable medium, wherein said computer subroutine is configured to:
subdivide a two-dimensional project image that is to be displayed from the two-dimensional projection images into a grid pattern having a plurality of parcels in a perfusion region of the examination object, wherein each of the parcels has a predetermined shape and each parcel includes a plurality of pixels,
determine a characteristic value for each parcel in the perfusion region,
determine a projection color for the each parcel based on the characteristic value,
assign the projection color to the each parcel, and
represent the each parcel by the assigned projection color.

18. The computer program as claimed in claim 17, wherein the characteristic value is determined based on pixel values occurring in the each parcel of the two-dimensional projection image or differences of pixel values of the each parcel between the two-dimensional projection image and another two-dimensional projection image from the two-dimensional projection images, and
wherein the pixel values are determined by at least essentially locally identical areas of the examination object.

19. A medical examination device for representing two-dimensional projection images of an examination object showing a variation of a distribution of a contrast medium over time in the examination object, comprising:
an image recording device that records the two-dimensional projection images; and
a computer that:
subdivides a two-dimensional project image that is to be displayed from the two-dimensional projection images into a grid pattern having a plurality of parcels in a perfusion region of the examination object, wherein each of the parcels has a predeteimined shape and each parcel includes a plurality of pixels,
determines a characteristic value for each parcel in the perfusion region,
determines a projection color for the each parcel based on the characteristic value,
assigns the projection color to the each parcel, and
represents the each parcel by the assigned projection color.

20. The device as claimed in claim 19, wherein the characteristic value is determined based on pixel values occurring in the each parcel of the two-dimensional projection image or differences of pixel values of the each parcel between the two-dimensional projection image and another two-dimensional projection image from the two-dimensional projection images, and
wherein the pixel values are determined by at least essentially locally identical areas of the examination object.

* * * * *